United States Patent [19]

Kappler et al.

[11] 4,234,502

[45] Nov. 18, 1980

[54] METHOD OF PREPARING AMINOALKYLSILANES

[75] Inventors: Fritz-Robert Kappler, Troisdorf; Claus-Dietrich Seiler, Rheinfelden, both of Fed. Rep. of Germany

[73] Assignee: Dynamit Nobel Aktiengesellschaft, Troisdorf, Fed. Rep. of Germany

[21] Appl. No.: 961,311

[22] Filed: Nov. 16, 1978

[30] Foreign Application Priority Data

Nov. 29, 1977 [DE] Fed. Rep. of Germany ....... 2753124

[51] Int. Cl.$^3$ ............................ C07F 7/10; C07F 7/18
[52] U.S. Cl. .................................................. 556/413
[58] Field of Search .................. 260/448.8 R, 448.2 E

[56] References Cited

U.S. PATENT DOCUMENTS 3,621,047  11/1971  Golitz et al. ................. 260/448.8 R
4,045,460   8/1977  Kleinstück ................... 260/448.8 R
4,064,155  12/1977  Speier ......................... 260/448.8 R

*Primary Examiner*—Paul F. Shaver
*Attorney, Agent, or Firm*—Sprung, Felfe, Horn, Lynch & Kramer

[57] ABSTRACT

An improved process for the production of an aminoalkylsilane by reaction of a chloroalkylsilane with ammonia or alkylamine at an elevated temperature or pressure wherein the chloroalkylsilane is added in a less than stoichiometric ratio to the ammonia or alkylamine preheated in a pressure vessel at a temperature between 50° and 200° C. Thereafter the reaction is carried out in a known manner within the temperature range of 50° to 200° C. By this manipulative technique, a higher yield of aminoalkylsilane is obtained per unit of time and the aminoalkylsilane is obtained in a greater purity.

8 Claims, No Drawings

METHOD OF PREPARING AMINOALKYLSILANES

BACKGROUND OF THE INVENTION

1. Field of the Invention

This invention relates to a process for preparing aminoalkylsilanes by contacting chloroalkylsilanes with ammonia or a lower alkylamine under pressure at an elevated temperature. More especially, this invention relates to the preparation of aminoalkylalkoxysilanes by reaction of chloroalkylalkoxysilanes with ammonia or a lower alkylamine under elevated temperature and pressure. More especially, this invention relates to an improved manipulative technique for effecting the reaction whereby production of impurities is minimized and the desired product is obtained in a greater volume-time yield.

2. Discussion of the Prior Art

Broadly, it is known to prepare aminoalkylsilanes by reaction of chloroalkylsilanes and ammonia and at an elevated temperature and pressure. Such is described, for instance, in U.S. Pat. No. 2,832,754. According to the process therein disclosed, which is useful for the preparation of aminoalkylalkoxysilanes, reactants are together placed in a pressure vessel which is then closed and heated to a temperature of at least 90° C. According to the disclosure of the aforenoted Patent, the reaction necessarily producing bis-(alkoxysilylalkyl)-amines of the general formula

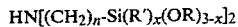

and tris-(alkoxysilylalkyl)-amines of the formula

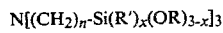

where n=1 to 3, x=0, 1 or 2, R' is methyl and R is alkyl of 1 to 3 carbon atoms (as by-products). The formation of these secondary and tertiary amines is explainable by the fact that a portion of the chloroalkylalkoxysilane reactant reacts with formed primary amine resulting in production of these bis and tris by-products.

According to the patent, formation of these by-products can be minimized by using a great excess of ammonia. However, even with a twenty-fold molar excess of ammonia, the yields of primary amines, i.e., desired products such as γ-aminopropyltriethoxysilane, are only around 50%.

It is therefore a problem of providing ω-aminoalkylsilanes, especially ω-aminoalkylalkoxysilanes by reaction of the corresponding chloroalkylsilanes and ammonia or lower alkylamines without the formation of substantial quantities of secondary and tertiary amines. It is an object of this invention, therefore, to provide a process whereby such aminoalkylsilanes and aminoalkylalkoxysilanes can be provided at high volume-time yields by reaction of the corresponding chloroalkylsilanes and ammonia or a lower alkylamine. It is a further object of this invention, therefore, to provide such a process whereby the yields of primary aminoalkylsilanes are increased with concomitant decrease in the yields of secondary and tertiary amines. It is still a further object of this invention to provide such a process which can be carried out at more moderately elevated temperatures than required according to the Patent aforenoted.

SUMMARY OF THE INVENTION

In accordance with this invention, the aforesaid desideratum is satisified by an improved process for the preparation of aminoalkylsilanes, especially aminoalkylalkoxysilanes by reaction of chloroalkylsilanes with ammonia or lower alkylamine under elevated temperature and pressure. In accordance with the process of the invention, the chloroalkylsilane reactant is added in less than stoichiometric ratio to liquid ammonia or alkylamine contained in a pressure vessel at an elevated pressure and at a temperature between 50° and 200° C. After addition of the chloroalkylsilane, the reaction is completed in known manner. The temperature of the reaction mixture is maintained in the range of between 50° and 200° C.

Generally, the process is conducted in a pressure vessel such as a closed autoclave wherein elevated pressure is maintained owing to the temperature of the reaction mixture.

It has furthermore been found desirable to stir the reaction mixture during the reaction, so as to produce a uniform blend of the chloroalkylalkoxysilane and the liquid ammonia. The use of additional solvents is thereby rendered unnecessary.

When the method of the invention is applied, it has surprisingly been found that the production of by-product is lower than it is in the method of U.S. Pat. No. 2,832,754. Furthermore, however, the method of the invention has the additional advantage that it makes it possible to operate at temperatures below 90° C. These relatively low temperatures are not suitable, according to U.S. Pat. No. 2,832,754 for the reaction of chloropropyltriethoxysilane with ammonia for the preparation of γ-aminopropyltriethoxysilane.

Furthermore, the procedure of the invention enables the reaction time to be reduced by more than one-fourth in comparison with the known method, even when the reaction is performed at temperatures far below the range employed in the known methods.

The procedure of the invention can be performed not only with ammonia but also with methylamine or ethylamine as one of the two reactants. The amine or the ammonia is placed in the autoclave and heated under pressure at temperatures between 50° and 200° C. The preferred temperature range is between 50° and 90° C. It is desirable, furthermore, to heat the amine or ammonia to the temperature at which the reaction with the chloroalkylsilane is then to take place. This reaction is performed preferably also at temperatures between 50° and 90° C.

The preferred reactant is ammonia although lower alkylamines can also be employed. Lower alkylamines particularly contemplated are primary amines where the alkyl group is 1 to 8 carbon atoms preferably 1 to 4 carbon atoms. Especially contemplated, are methyl and ethyl amines.

The chloroalkylalkoxysilane which is usable as starting product is to be of the formula,

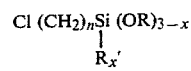

wherein R represents an alkyl moiety of one to three carbon atoms, R' can be a methyl moiety, n can assume values between 1 and 3, and x=0 or 1 or 2. The compounds to be preferred are the chloroalkyltrialkoxysilanes in which x, therefore, is equal to 0.

The amount of the chloroalkylsilane is to be in a lower than stoichiometric ratio to the ammonia or alkylamine. The molar ratio of the ammonia or alkylamine to the chloroalkylsilane is accordingly to be between 100:1 and 10:1, preferably between 80:1 and 20:1. A greater excess of ammonia or alkylamine is also possible in accordance with the invention, but if offers no further advantages. The greater the excess of ammonia or alkylamine is, the lower will be the percentage of the by-products. The by-product content, however, will always be lower than in the method of U.S. Pat. No. 2,832,754, if one sets out with the same ratio of ammonia to γ-chloropropyltrialkoxysilane.

The optimum ratio of ammonia to chloroalkylsilane will depend on the desired quality of the aminoalkylsilane and the processing capacity of the apparatus as a whole. A slight excess of ammonia or monoalkylamine has the advantage that a higher absolute amount of product can be obtained per unit of volume of the reactants, and its separation from the unreacted ammonia or alkyl amine is easier on account of the smaller amounts. On the other hand, however, the production of by-products is so great that they would constitute an unacceptable drawback on the entire process unless they could be utilized.

In general, however, the reaction is performed with as great as possible an excess of ammonia or monoethylamine.

Any pressure reactor is suitable, but the size should be such that it will be substantially filled with liquid under the reaction conditions so that only a small amount of ammonia or alkylamine can evaporate and the reaction will take place in the liquid phase. The pressure is established by the gas pressure of the evaporated ammonia or alkylamine. No additional pressure increase is necessary.

It is advantageous to allow the chloroalkylsilane that is injected into the reactor to react completely. In general this will be the case in six to eight hours at a reaction temperature of 75° C. After the reaction has ended, the reactor is relieved of pressure and the excess ammonia or alkylamine is allowed to evaporate. After condensation it can be recycled to the next batch.

The raw product freed of the excess ammonia or alkylamine must then be filtered to remove the ammonia chloride or amine chloride that has formed during the reaction. The desired aminoalkylalkoxysilane is separated from the filtrate by vacuum distillation. The secondary and tertiary amines will remain in the sump and, if desired, they too can be separated by vacuum distillation and recovered.

In order to more fully illustrate the nature of the invention and in a manner of practicing the same, the following examples are presented. The examples include one example (Example 2) for purposes of comparison. It will be noted that the process of the invention provides the desired product in higher yields.

EXAMPLES

EXAMPLE 1

Into a ten-liter steel autoclave with stirrer, 3400 g (200 moles) of liquid ammonia was poured, and the reactor was sealed. Then the ammonia was heated to 75° C., causing a pressure of 36 bars to be established. After this temperature was reached, γ-chloropropyltriethoxysilane was fed in, with stirring at 183 rpm, for a period of one hour, in the amount of 2.67 moles; then stirring was continued for 8 hours at 75° C. Then the pressure was let off and the ammonia was removed. After the removal of ammonium chloride by filtration, the remaining raw product was purified by vacuum distillation. From the 642 grams of γ-chloropropyltriethoxysilane, 486 g of γ-aminopropyltriethoxysilane was obtained (82.4% of the theoretical yield) plus 98.3 g of byproducts (secondary and tertiary amines).

EXAMPLE 2 (For purposes of comparison)

601 g of γ-chloropropyltriethoxysilane (2.5 moles) and 3190 g (187.5 moles) of liquid ammonia were poured into the autoclave of Example 1. The vessel was sealed and heated for 8.5 hours at 100° C. Then the reactor was cooled and the excess ammonia was removed by evaporation.

Ammonium chloride was filtered out of the remaining liquid and the filtrate was subjected to fractional distillation. 410 g (=74.2%) of γ-aminopropyltriethoxysilane and 121 g of secondary and tertiary amine were obtained.

EXAMPLE 3

The the same autoclave as in Example 1, 3400 g (200 moles) of liquid ammonia was placed, the autoclave was sealed and the temperature was raised to 75° C. After this temperature was reached, 962 g (4 moles) of γ-chloropropyltriethoxysilane was added with stirring at 585 rpm. The rest of the procedure was the same as in Example 1.

695.2 g of γ-aminopropyltriethoxysilane was obtained by distillation (78.8% of the theory). The amount of the byproducts was 179.8 grams.

EXAMPLE 4

The procedure was the same as in Example 3, but 1205 g (5 moles) of γ-chloropropyltriethoxysilane was added to the ammonia after the latter had been sealed in the autoclave and heated to 75° C., so that the molar ratio of ammonia to chloropropyltriethoxysilane was 40:1.

839 g of γ-aminopropyltriethoxysilane was obtained (76.1%) plus 252 g of secondary and tertiary amines.

EXAMPLE 5

The procedure was the same as in Example 3, except that 1800 g (7.5 moles) of γ-chloropropyltriethoxysilane was added to 2550 g (=150 moles) of ammonia which had been heated to 100° C.; the molar ratio of ammonia to chloropropyltriethoxysilane was accordingly 20:1.

958 g of γ-aminopropyltriethoxysilane (57.9% of the theory) was obtained, plus 661 g of secondary and tertiary amines.

What is claimed is:

1. In a method of preparing an aminoalkylsilane by contacting a chloroalkylsilane with ammonia or an alkylamine at a an elevated temperature under pressure, the improvement which comprises introducing the chloroalkylsilane in a less than stoichiometric ratio to the ammonia or alkylamine preheated in a pressure vessel at a temperature between 50° and 200° C. and thereafter carrying out the reaction at a temperature between 50° and 200° C.

2. A process according to claim 1 wherein the reaction mixture is stirred.

3. A process according to claim 1 wherein the process is performed at a temperature between 50° and 90° C.

4. A process according to claim 1 wherein the chloroalkylsilane reactant is a chloroalkyl alkoxysilane.

5. A process according to claim 4 wherein the chloroalkylalkoxysilane has the formula $$Cl(CH_2)_nSi(OR)_{3-x}R'_x$$

wherein R represents an alkyl moiety of 1 to 3 carbon atoms, R' represents a methyl radical, n is a value between 1 and 3 and x is 0, 1 or 2.

6. A process according to claim 1 wherein the chloroalkylsilane is one having the formula $$Cl(CH_2)_nSi(OR)_3$$

wherein R represents an alkyl moiety of 1 to 3 carbon atoms and n represents 1,2 or 3.

7. A process according to claim 1 wherein the chloroalkylsilane is added to ammonia.

8. A process according to claim 1 wherein the chloroalkylsilane is added to an alkylamine.